United States Patent [19]

Liu et al.

[11] 4,213,966

[45] Jul. 22, 1980

[54] METHOD FOR ISOLATING POLYETHER ANTIBIOTICS

[75] Inventors: Wen-Chih Liu, Princeton Junction; William E. Brown; Gail L. Astle, both of Princeton, all of N.J.

[73] Assignee: E. R. Squibb & Sons, Inc., Princeton, N.J.

[21] Appl. No.: 802,768

[22] Filed: Jun. 2, 1977

[51] Int. Cl.² .................. A61K 35/00; C07H 15/22
[52] U.S. Cl. ............................ 424/123; 536/17 R
[58] Field of Search ............... 424/123, 122; 536/17

[56] References Cited

U.S. PATENT DOCUMENTS

| | | | |
|---|---|---|---|
| 3,476,856 | 11/1969 | Kulbakh et al. | 424/123 |
| 3,873,693 | 3/1975 | Meyers et al. | 424/122 |

OTHER PUBLICATIONS

Omura et al., J. Antibiotics, XXIX, No. 1 (1976), pp. 15–20.

Primary Examiner—Jerome D. Goldberg
Attorney, Agent, or Firm—Lawrence S. Levinson; Burton Rodney

[57] ABSTRACT

A method is provided for recovering a polyether antibiotic, such as lonomycin, monensin or ionomycin from a fermentation broth, wherein the polyether is first extracted with a water-immiscible solvent, such as ethyl acetate, and the resulting extracts concentrated, dissolved in aqueous methanol and then extracted into hexane, benzene or mixtures thereof. The polyether is thereby recovered in crystalline form directly from the latter extract.

8 Claims, No Drawings

METHOD FOR ISOLATING POLYETHER ANTIBIOTICS

FIELD OF THE INVENTION

The present invention relates to a simple, efficient method for isolating polyethers, such as lonomycin, monensin and ionomycin from fermentation broths.

BACKGROUND OF THE INVENTION AND DISCUSSION OF PRIOR ART

Although the polyether antibiotics were first described more than twenty-five years ago, the therapeutic potential of this antibiotic class was not appreciated until 1968 when the anticoccidial activity of monensin was reported. The subsequent commercial use of monensin for the treatment of avian coccidiosis and its development as a growth promoter in cattle led to the realization that other members of the class, including nigericin, lasalocid, salinomycin, laidlomycin and lonomycin also have therapeutic potential.

Utilization of these agents in agriculture as feed additives for the treatment of disease in poultry and for the enhancement of growth in ruminants requires that they be available at a relatively low cost. Thus, the fermentation must be capable of producing the antibiotic in high yield and, in addition, isolation of product must be conducted simply and efficiently. The published procedures for the isolation of polyether antibiotics are multistep operations involving column chromatography.

Thus, for example, U.S. Pat. No. 3,873,693 to Meyers et al discloses the antibiotic ionomycin and a technique for recovering same from the fermentation broth by filtering off the mycelium, extracting the filtrate with a lower alkanol like butanol, or a lower alkyl ester like ethyl acetate or butyl acetate, or a hydrocarbon like chloroform or a lower alkyl ketone like methyl isobutyl ketone. The organic phase is concentrated to a syrup; the purified product is obtained by column chromatography.

Omura et al in a paper entitled "Isolation of a New Polyether Antibiotic, Lonomycin", J. Antibiotics, XXIX No. 1 (1976), pp 15-20, describe a technique for isolation and purification of lonomycin as follows. The mycelia is centrifuged from the fermentation broth and extracted with ethyl acetate. The ethyl acetate extract is separated from the aqueous layer and concentrated in vacuo below 50° C. to give a brown syrup. The syrup is extracted three times with benzene. The resulting extract is recovered, evaporated to dryness, and the residue is extracted three times with methanol. The extracts are concentrated in vacuo to give a partially purified antibiotic in the form of a yellow syrup. The syrup is dissolved in benzene and subjected to column chromatography to give a white powder which is recrystallized from n-hexane to give lonomycin.

Similar expensive and time-consuming multistep isolation procedures including column chromatography are required in the recovery of monensin and other polyether antibiotics from fermentation broths.

Thus, it is seen that a long felt need exists for a simple, efficient method for isolating polyether antibiotics of high purity.

DESCRIPTION OF THE INVENTION

In accordance with the present invention, a simple, efficient method is provided for isolating a polyether antibiotic from its fermentation broth, which method includes the steps of adjusting the pH of the filtrate (obtained by filtering fermentation broth) to a slightly basic pH, extracting the filtrate with a water-immiscible organic solvent, such as a lower alkyl ester, for example, ethyl acetate or butyl acetate; a lower alkanol, for example, butanol; a chlorinated solvent, for example, chloroform; a lower alkyl ketone, for example, methyl isobutyl ketone; or benzene. The organic phase is concentrated to a thick syrup. The syrup is then dissolved in a water-miscible organic solvent, such as a lower alkanol, for example methanol. The pH of the resulting solution is adjusted upwards to from about 9 to about 14, preferably 11 to 13. Water is added and the mixture is extracted with an inert solvent, such as pentane, hexane, heptane, ligroin, petroleum ether or similar solvent. Upon concentration of the latter extract, the polyether antibiotic crystallizes out. The solid may then be further purified by recrystallization.

In carrying out the above method where ionomycin is to be isolated, the aqueous-lower alkanol solution of the ethyl acetate (or other water-immiscible solvent) concentrate (pH adjusted to 9-14, preferably 11 to 13) is first extracted with a mixture of benzene-hexane or other solvent as described hereinafter, and the residue is redissolved in aqueous-lower alkanol solvent; the solution is readjusted to pH 9-14, preferably 11 to 13, and then extracted with the inert solvent (for example, hexane) to separate ionomycin.

However, in each of the above procedures, the polyether antibiotic is obtained in pure crystalline form directly from the extracts without the need for column chromatography or other expensive time-consuming purification techniques.

The method of the invention is applicable to the isolation and purification of polyether antibiotics, such as lonomycin, monensin, ionomycin, as well as nigericin, lasalocid, salinomycin and laidlomycin, and other known polyether antibiotics, with the methods applicable to lonomycin and monensin, and ionomycin being preferred.

In carrying out the method of the invention, the pH of the filtrate obtained from the filtering of the fermentation broth is adjusted with the addition of NaOH, KOH, NH$_4$OH, or other alkaline solution to a slightly basic pH ranging from about 7.2 to about 8. It is desirable to keep the pH at this stage at 8 or below in order to avoid premature precipitation of the polyether.

The slightly basic filtrate is then extracted with any of the water-immiscible organic solvents as listed hereinbefore, with ethyl acetate being preferred. The volume ratio of solvent to filtrate will generally range from about 2:1 to about 1:5 and preferably 1:1 to 1:3, and optimally 1:2, with the extraction being carried out 1 to 4 times and preferably 2 to 3 times.

The concentrated organic phase extract will then be dissolved in the lower alkanol, preferably in methanol or ethanol. The pH of the solution is then adjusted by the addition of a strong base, such as sodium hydroxide, potassium hydroxide, and the like, to 9 to 14.

In the case of lonomycin and monensin, after water is added to increase the volume of the solution from 1.5 to 3 fold, preferably to 2 fold, the protic inert solvent, preferably hexane, is added in an amount of from about 50 to about 200% and preferably about 100% by volume of the mixture. The hexane extraction is repeated from 3 to 8 times and preferably from 4 to 6 times. Upon concentration of the extracts, crystalline polyether forms without the need for column chromatography or other involved separation procedures.

Where ionomycin is to be extracted, the aqueous-organic phase of pH 9 to 14, preferably 11 to 13, is first extracted with benzene-hexane (1:1 to 1.5:1) or benzene, chlorinated hydrocarbons, such as chloroform, dichloromethane, carbon tetrachloride, or other similar solvent, or mixtures thereof, in a volume ranging from about 50 to about 200%, and preferably about 100% of the aqueous-organic phase. This extraction is carried out from 3 to 8 times and preferably from 4 to 6 times. The residues obtained from such extractions are redissolved in lower alkanol, the pH thereof is adjusted to 9 to 14, preferably 11 to 13, by the addition of strong base as described above and water is added to increase the volume thereof to 2 fold. The hexane extraction step is then carried out as described above and crystalline ionomycin is recovered from the concentrated extracts without the need for expensive separating procedures.

The following Examples represent preferred embodiments of the present invention.

EXAMPLE 1

Isolation of Lonomycin

The broth filtrate from a 250-1 fermentation of *Streptomyces ribosidificus*, strain TM481, is adjusted to pH 7.5 and extracted twice each with 120-1 of ethyl acetate. The ethyl acetate extracts are combined and concentrated in vacuo to a thick syrup. The syrup is then dissolved in 300 ml methanol and the solution adjusted to pH 12 with 5 N NaOH. Three hundred ml water is added and the mixture is extracted with 600 ml n-hexane three times. Upon concentration of the combined hexane extracts to a small volume, crystalline lonomycin is obtained.

The solid is separated from the mother liquor by filtration, followed by recrystallization from an acetone-hexane mixture. The final yield of pure lonomycin is approximately 25 g, m.p. 188°–189° C.

Comparison of the isolated sample with an authentic sample of lonomycin shows that the m.p., C-H analysis, I.R. and N.M.R. spectra are essentially identical. The efficiency of the procedure is substantiated by thin layer chromatographic studies which indicate that essentially no lonomycin is left in the aqueous layers after extraction with either ethyl acetate or hexane.

EXAMPLE 2

Isolation of Monensin

The broth filtrate from a 10-1 fermentation of *Streptomyces cinnamonensis*, ATCC 15,413 is adjusted to pH 7.5 and extracted twice each with 5-1 of ethyl acetate. The ethyl acetate extracts are combined and concentrated in vacuo to a thick syrup. The syrup is then dissolved in 30 ml methanol and the solution adjusted to pH 12 with 5 N NaOH. Thirty ml water is added and the mixture is extracted with 60 ml n-hexane three times. Upon concentration of the combined hexane extracts to a small volume, crystalline monensin is obtained.

The solid is separated from the mother liquor by filtration, followed by recrystallization from an acetone-hexane mixture. The final yield of pure monensin is approximately 200 mg, m.p. 272°–274° C.

By thin layer chromatography on silica gel plate with a solvent system of 2.5% methanol in $CHCl_3$, only one component is found, with an $R_f$ value identical to that of the monensin standard. Furthermore, the I.R. spectrum of the isolated material is identical to that published for monensin. Again, thin layer chromatographic studies confirm that the monensin is extracted nearly quantitatively into ethyl acetate from the broth filtrate and into hexane from the 50% aqueous methanol.

EXAMPLE 3

Isolation of Ionomycin

The harvest broth of a 250-1 batch of *Streptomyces conglobatus* ATCC 31,005 is filtered and the filtrate extracted twice with 0.5 volume of ethyl acetate.

The ethyl acetate concentrate is dissolved in 400 ml methanol and the solution adjusted to pH 12 with 5 N NaOH, and 400 ml water is added. The mixture is extracted with 800 ml benzene-hexane (1:1) five times. The benzene-hexane extracts are combined and concentrated to dryness. The residue is redissolved in 200 ml methanol and the solution adjusted to pH 12 with 5 N NaOH, and 200 ml water is added. The resulting mixture is extracted with 400 ml hexane five times. The hexane extracts are combined and concentrated in vacuo to a small volume, yielding crystalline ionomycin. Upon recrystallization from acetone-hexane, approximately 12 g of the pure compound, m.p. 203° C. is obtained. It proves to be pure ionomycin on comparison with an authentic sample by conventional physical chemical methods.

What is claimed is:

1. A method for isolating a polyether antibiotic selected from the group consisting of lonomycin, monensin, ionomycin, nigericin, lasalocid, salinomycin, and laidlomycin from its fermentation broth, which comprises adjusting the filtrate obtained from filtering of the fermentation broth to a slightly basic pH of within the range of from about 7.2 to about 8, extracting said filtrate with a water-immiscible organic solvent selected from the group consisting of ethyl acetate, butyl acetate, butanol, chloroform, methyl isobutyl ketone and benzene, said water-immiscible organic solvent being employed in a volume ratio to the filtrate of within the range of from about 2:1 to about 1:5, with the extraction being carried out 1 to 4 times; dissolving a concentrated form of the resulting organic phase in an aqueous lower alkanol solvent selected from the group consisting of methanol and ethanol; adjusting the pH of the resulting solution upwards to from about 9 to about 14; adding water to increase the volume of the solution from 1.5 to 3 fold; extracting the solution with a protic solvent selected from the group consisting of pentane, hexane, heptane, ligroin, and petroleum ether; and concentrating the resulting organic phase thereby causing the polyether antibiotic to crystallize out.

2. The method as defined in claim 1 wherein said polyether antibiotic is lonomycin or monensin.

3. The method as defined in claim 1 wherein said solvent is ethyl acetate.

4. The method as defined in claim 1 wherein said protic solvent is hexane.

5. The method as defined in claim 1 including the step of extracting the solution of the organic phase in a lower alkanol solvent said solution having a pH ranging from about 9 to about 14, with a mixture of benzene and hexane in a weight ratio of benzene to hexane of within the range of from about 1:1 to about 1.5:1, redissolving the resulting organic phase in methanol or ethanol and readjusting the pH thereof to within the range of from about 9 to about 14 prior to extracting same with said protic solvent.

6. The method as defined in claim 5 wherein said polyether antibiotic is ionomycin.

7. The method as defined in claim 5 wherein said water-immiscible solvent is ethyl acetate.

8. The method as defined in claim 5 wherein said protic solvent is hexane.

* * * * *